(12) United States Patent
Vargo et al.

(10) Patent No.: US 6,613,208 B2
(45) Date of Patent: Sep. 2, 2003

(54) ONE-PIECE HARNESS AND UPPER SHIELD DESIGN AND THE METHOD OF MAKING THE SAME

(75) Inventors: James P. Vargo, Swartz Creek, MI (US); Robert Gregory Kechner, Davison, MI (US); Charles Scott Nelson, Clio, MI (US)

(73) Assignee: Delphi Technologies, Inc., Troy, MI (US)

( * ) Notice: Subject to any disclaimer, the term of this patent is extended or adjusted under 35 U.S.C. 154(b) by 221 days.

(21) Appl. No.: 09/782,175

(22) Filed: Feb. 13, 2001

(65) Prior Publication Data
US 2002/0134678 A1 Sep. 26, 2002

(51) Int. Cl.$^7$ ............................................. G01N 27/407
(52) U.S. Cl. ........................... 204/428; 29/422; 29/428; 29/505; 29/506; 29/521; 29/592.1; 204/426
(58) Field of Search ................................. 204/421–429; 29/422, 428, 505, 506, 521, 592.1

(56) References Cited

U.S. PATENT DOCUMENTS

| | | | | |
|---|---|---|---|---|
| 3,960,693 A | * | 6/1976 | Weyl et al. |
| 4,362,609 A | * | 12/1982 | Sano et al. |
| 5,089,133 A | * | 2/1992 | Kato et al. |
| 5,759,365 A | * | 6/1998 | Yamada et al. |
| 5,785,829 A | * | 7/1998 | Watanabe |
| 6,068,746 A | * | 5/2000 | Kojima et al. |
| 6,179,989 B1 | * | 1/2001 | Kennard et al. |
| 6,342,141 B1 | * | 1/2002 | Nelson |

* cited by examiner

Primary Examiner—T. Tung
(74) Attorney, Agent, or Firm—Patrick M. Griffin

(57) ABSTRACT

An exhaust gas sensor is provided and formed by attaching the sensor's upper shield and shell. The attachment is attained by bending a protruding segment or lip over a terminal end portion of the lower shield. This produces a single sealing surface and eliminates the requirement of a conventional crimp which places high compressive forces on the sensing element.

16 Claims, 2 Drawing Sheets

ONE-PIECE HARNESS AND UPPER SHIELD DESIGN AND THE METHOD OF MAKING THE SAME

TECHNICAL FIELD

The present invention relates to exhaust gas sensors. More particularly, the present invention relates to an exhaust gas sensor with a crimp design.

BACKGROUND OF THE INVENTION

Exhaust gas sensors are used in a variety of applications that require qualitative and quantitative analysis of gases. For example, exhaust gas sensors have been used for many years in automotive vehicles to sense the presence of oxygen in exhaust gases, for example, to sense when an exhaust gas content switches from rich to lean or lean to rich. In automotive applications, the direct relationship between oxygen concentration in the exhaust gas and the air-to-fuel ratios of the fuel mixture supplied to the engine allows the exhaust sensor to provide oxygen concentration measurements for determination of optimum combustion conditions, maximization of fuel economy, and the management of exhaust emissions.

A conventional stoichiometric sensor typically consists of an ionically conductive solid electrolyte material, a porous electrode on the sensor's exterior exposed to the exhaust gases with a porous protective overcoat, and a porous electrode on the sensor's interior surface exposed to a known gas partial pressure. Sensors typically used in automotive applications use a yttria stabilized zirconia based electrochemical galvanic cell with porous platinum electrodes, operating in potentiometric mode, to detect the relative amounts of oxygen present in an automobile engine's exhaust. When opposite surfaces of this galvanic cell are exposed to different oxygen partial pressures, an electromotive force is developed between the electrodes on the opposite surfaces of the zirconia wall, according to the Nernst equation:

$$E = \left(\frac{-RT}{4F}\right) \ln\left(\frac{P_{O_2}^{ref}}{P_{O_2}}\right)$$

where:

$E$ = electromotive force $R$ = universal gas constant $F$ = Faraday constant $T$ = absolute temperature of the gas $P_{O_2}^{ref}$ = oxygen partial pressure of the reference gas $P_{O_2}$ = oxygen partial pressure of the exhaust gas Due to the large difference in oxygen partial pressures between fuel rich and fuel lean exhaust conditions, the electromotive force changes sharply at the stoichiometric point, giving rise to the characteristic switching behavior of these sensors. Consequently, these potentiometric sensors indicate qualitatively whether the engine is operating fuel rich or fuel lean, without quantifying the actual air to fuel ratio of the exhaust mixture.

As taught by U.S. Pat. No. 4,863,584 to Kojima et al., U.S. Pat. No. 4,839,018 to Yamada et al., U.S. Pat. No. 4,570,479 to Sakurai et al., and U.S. Pat. No. 4,272,329 to Hetrick et al., a sensor which operates in a diffusion limited current mode produces a proportional output which provides a sufficient resolution to determine the air-to-fuel ratio under fuel-rich or fuel-lean conditions. Generally, diffusion limited current sensors have a pumping cell and a reference cell with a known internal or external oxygen partial pressure reference. A constant electromotive force, typically corresponding to the stoichiometric electromotive force, is maintained across the reference cell by pumping oxygen through the pumping cell. The magnitude and polarity of the resulting diffusion limited current is indicative of the exhaust oxygen partial pressure and, therefore, a measure of air-to-fuel ratio.

Where a gas-diffusion-limiting means is added to an oxygen pump, the pump current can be limited, and the limiting current is linearly proportional to the absolute value of the equilibrium oxygen concentration of the exhaust gas. In lean condition, the equilibrium oxygen concentration is larger than zero, which indicates a surplus of oxygen, and oxygen needs to be pumped out of the exhaust gas to create a limiting current. In the rich condition, the equilibrium oxygen concentration is smaller than zero, which indicates depletion of oxygen, and oxygen needs to be pumped into the exhaust gas to create a limiting current. Therefore, using the absolute value and the polarity of the limiting current, one can determine the air-to-fuel ratio of the exhaust gas.

However, an oxygen pump cell will not switch its current polarity automatically if both pump electrodes are exposed to the same exhaust gas. Conventional sensor technology either uses an air reference electrode as one of the pump electrodes or utilizes an air reference electrode as a third electrode to detect the lean or rich status of the exhaust gas (by emf mode) and to switch the current polarity accordingly. In this way, wide range air-to-fuel ratios of the exhaust gas can be determined.

Such conventional sensors use two types of air reference electrodes. The first type has a sizable air chamber to provide oxygen from an ambient air supply to the reference electrode (breatheable air reference). However, to avoid contamination by the exhaust gas, the air chamber requires a hermetic seal sensor package, which is expensive and is problematic in field applications. The second type is a pumped-air reference electrode. It uses a pump circuit to pump oxygen from the exhaust gas to the reference electrode. As such, it does not require a sizable air chamber connected to ambient air.

One known type of exhaust sensor includes a flat plate sensor formed of various layers of ceramic and electrolyte materials laminated and sintered together with electrical circuit and sensor traces placed between the layers in a known manner. The flat plate sensing element can be both difficult and expensive to package within the body of the exhaust sensor since it generally has one dimension that is very thin and is usually made of briffle materials. Consequently, great care and time consuming effort must be taken to prevent the flat plate sensing element from being damaged by exhaust, heat, impact, vibration, the environment, etc. This is particularly problematic since most materials conventionally used as sensing element supports, for example, glass and ceramics, typically have a high modulus of elasticity and cannot withstand much bending. Hence, great care and expense is expended in preventing manufacturing failures.

Accordingly, there remains a need in the art for a low cost, temperature resistant sensor package having an improved assembly and design.

SUMMARY OF THE INVENTION

The problems and disadvantages of the prior art are overcome and alleviated by the dead headed sealed air reference sensor and method preventing contamination of a sensor. The exhaust gas sensor comprises an upper shield having an upper shield first end and an upper shield second end; an inner shield positioned with a portion of the upper shield second end; a shell having a shell first end and a shell second end positioned about a portion of the inner shield, the shell first end has a projecting edge spaced apart from the inner shield, wherein a segment is formed between the projecting edge and the inner shield; a crimp formed from a bent portion of the projecting edge of the shell about a terminal end portion of the inner shield; a lower shield affixed to the shell second end; and a sensor element extending through and within the lower shield, the shell, and the upper shield.

The method of forming an exhaust gas sensor, comprises providing an upper shield having an upper shield first end and an upper shield second end; positioning an inner shield within a portion of the upper shield second end; placing a shell having a shell first end and a shell second end positioned about a portion of the inner shield, the shell first end has a projecting edge spaced apart from the inner shield, wherein a segment is formed between the projecting edge and the inner shield; forming a crimp by bending a portion of the projecting edge of the shell about a terminal end portion of the inner shield; affixing a lower shield to the shell second end; and extending a sensor element through and within the lower shield, the shell, and the upper shield.

The above-described and other features and advantages of the present invention will be appreciated and understood by those skilled in the art from the following detailed description, drawings, and appended claims.

BRIEF DESCRIPTION OF THE DRAWINGS

The present invention will now be described by way of example with reference to the following Figure, which are meant to be exemplary, not limiting, and in which.

DESCRIPTION OF THE PREFERRED EMBODIMENT

Sensor shields and shells are typically crimped to adjoin the sections to form completed exhaust sensors. An exhaust sensor disclosed herein advantageously utilizes a crimp design. Typically, exhaust sensors are constructed to endure an exhaust gas environment while protecting the sensor components. Because of the sensor component fragility, the manufacturing process can be difficult and expensive. To preserve the components, a shield and shell are formed together to form a unitary sensor. To maintain a unitary structure, shields and shell are commonly adjoined together by, for example, crimping, welding, and/or adhesives.

Figure 1:
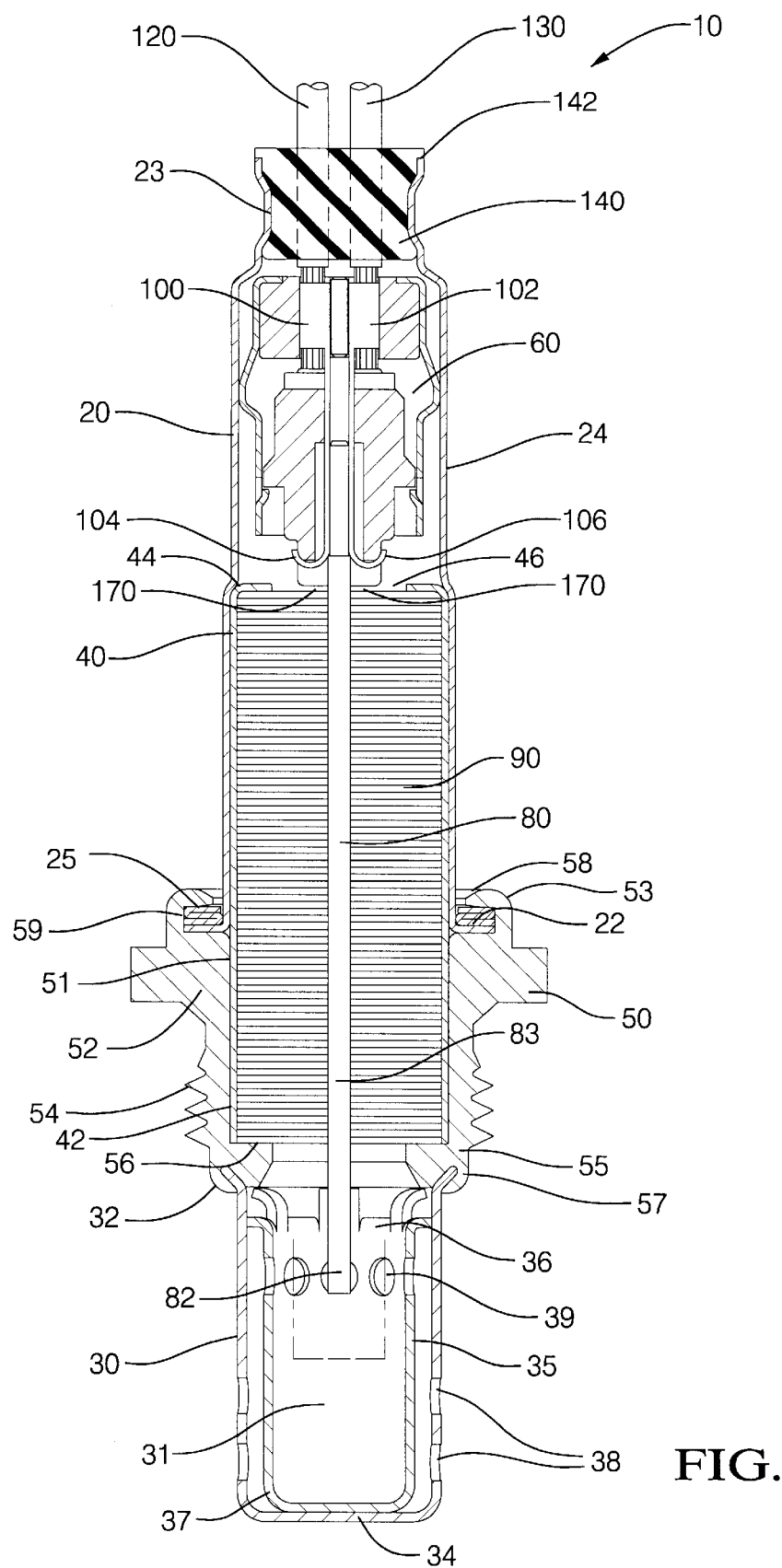
FIG. 1 is a cross-sectional side view of one embodiment of an exhaust sensor of the present invention utilizing a crimp.

Referring now to the FIG. 1, an exemplary exhaust sensor 10 is shown employing a crimp 58 of upper shield 20 to shell 50 in accordance with the present invention. Exhaust sensor 10 includes a housing structure generally formed of an upper shield 20 disposed above a shell 50. A lower shield 30 is disposed beneath shell 50. Inner shield 40 is optionally disposed within a lower portion of upper shield 20 and shell 50. A terminal connector 60 and a portion of a sensing element 80 are disposed within upper shield 20. Sensing element 80 is a pumped-air reference exhaust sensing element of a known type with any conventional geometry, such as a generally flat elongated rectangular shape. At a first end 82 thereof, sensing element 80 includes an exhaust constituent-responsive structure fabricated into sensing element 80 in a known manner, preferably along with a heater (not shown) of a known type.

Exhaust sensor 10 advantageously utilizes a crimp 58 to adhere upper shield 20 to shell 50. Crimp 58 is comprised of a first end 53 of shell 50 being disposed proximate to lower end 22 of the upper shield 20. First end 53 of shell 50 is formed as a projecting edge or lip of material spaced apart from inner shield 40 and shell inner edge 51 to form segment 59. Segment 59 is shown as a flat length, disposed substantially perpendicular to the length of upper shield 20, but can also comprise any angle. Lower end 22 of the upper shield 20 is formed so that a terminal end portion of lower end 22 is formed to extend at an angle from the main axis of sensing element 10 (i.e., at an angle from the sensing element 80), with a substantially perpendicular extension of the terminal end preferred. This terminal end portion of lower end 22 is then placed juxtaposition to segment 59 to rest thereupon. Segment 59 need be of sufficient length so that when crimp 58 is formed, it will engage the terminal end portion and hold it securely within the wrapped lip of first end 53. Optionally, a gasket 25, for example an S-gasket, can be used between the wrapped lip end of first end 53 and the terminal end of lower end 22. Gasket 25 can be formed as a separate piece of any suitable material for an exhaust environment. Alternatively, gasket 25 can be formed from the terminal end of lower end 22 by having the terminal end wrapped in and upon itself as a coiled, rolled, or layered section, or the like.

This crimping arrangement negates the need for a high pressure crimp of upper shield 20 to inner shield 40 and of shell 50 to inner shield 40 and creates only one sealing surface. For example, a prior art high pressure crimp required a pressure directed inward toward the sensor element of about 2,000 pounds per square inch (p.s.i.) whereas the crimping arrangement of the present invention uses a vertical pressure, i.e., pressure applied in a parallel direction to the sensor element, sufficient to dispose first end 53 inward, e.g., a pressure of about 10,000 p.s.i. to about 20,000 p.s.i., and more preferably between about 14,000 to about 16,000 p.s.i. As to the one sealing surface, this is formed between upper shield 20, shell 50, and inner shell 40. Whereas in the prior art, two sealing surfaces were created where shell 50 met inner shield 40 and where upper shield 20 met shell 50 (See FIG. 2).

Sensor 10 can be formed by known manufacturing techniques with the exception that upper shield 20 and components therein are mated to shell 50 and components therein so that the terminal end portion of lower end 22 is positioned juxtaposition to segment 59. Thereafter, a force is applied so that the wrapped lip of first end 53 is formed. This is particularly advantageous because the force used to form the wrapped lip is not directed inward towards sensor element 80. Instead, the force is directed in an approximately parallel or angled direction to the length of sensor element 80.

Figure 2:
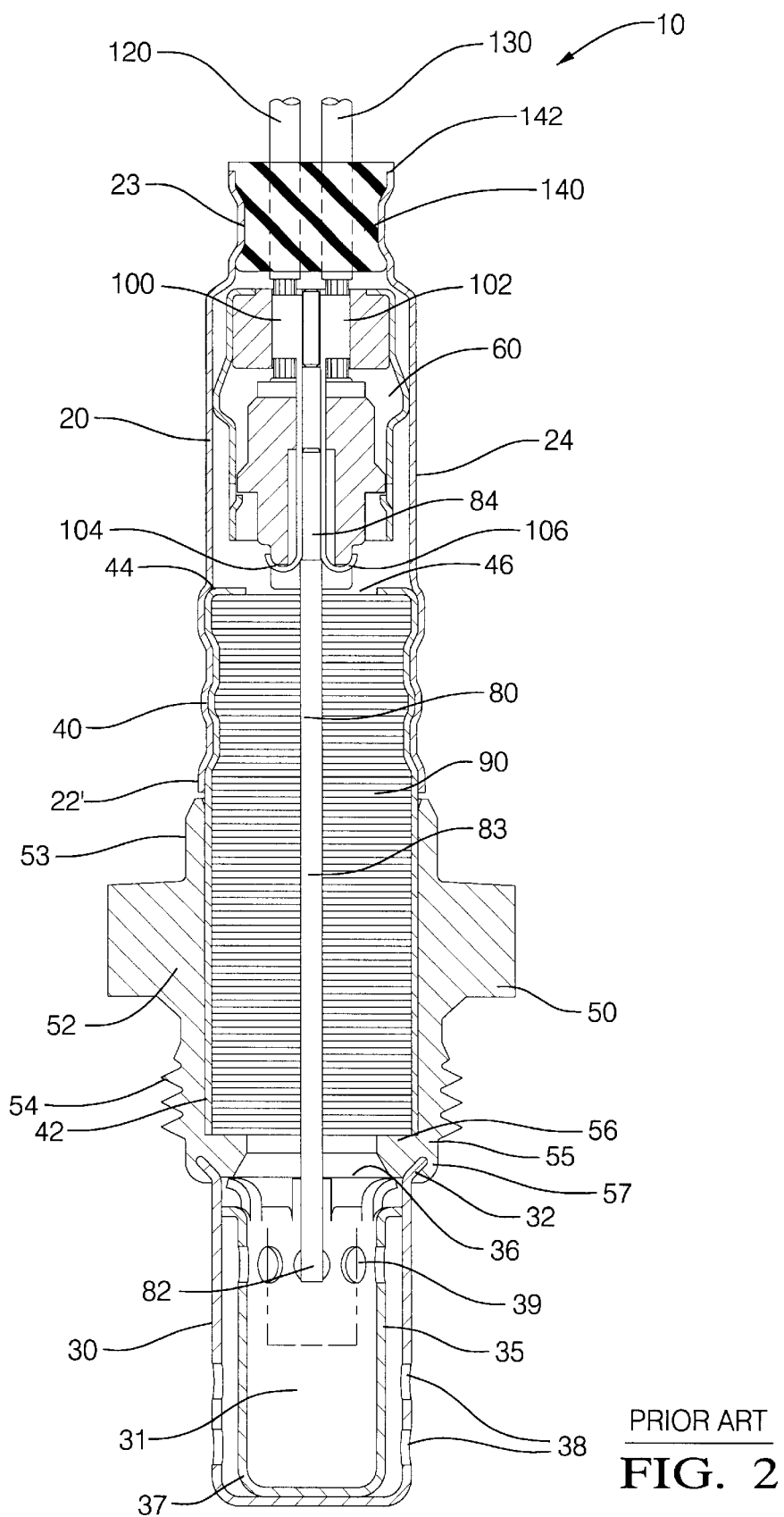
FIG. 2 is a prior art cross-sectional side view of an exhaust sensor utilizing a standard crimp.

Referring to prior art FIG. 2, first end 53 rests flatly against inner shield 40 to meet or to about meet the terminal end portion of lower end 22. Hence, a portion of inner shield 40 may be directly exposed to the exterior environment. The prior art sensor first end 53 does not form a projecting edge or lip of material to engage the terminal end of lower end 22. Therefore, the prior art assembly utilizes inward pressure crimps 85 to attach and retain upper shield 20 to inner shield 40 and to attach inner shield 40 to shell 50. The use of high pressure inward crimps by the prior art endanger the fragile sensor element 80 and thus increases the chance for failure and scrap due to the higher stresses placed upon the sensor.

Again referring to FIG. 1, as to the remaining structure of sensor 10, shell 50 includes a body portion 52 and a threaded portion 54 at a second end 55. Body portion 52 is preferably shaped to accommodate a wrench or other tool for tightening threaded portion 54 into a mount for an exhaust pipe or other component of an exhaust flow system enabling a sensor chamber 31 located within lower shield 30 to be located within a flow of exhaust gasses to be measured. Additionally, shell 50 is securely disposed around inner shield 40 and holds inner shield 40 via a compressive force engagement. Formed at second end 55 of shell 50 is a shoulder 56 for contacting first end 42 of inner shield 40, whereby inner shield 40 rests against shoulder 56 when shell 50 is secured to inner shield 40 during assembly.

At a second end 84 of sensing element 80, lower ends 104 and 106 of terminals 100 and 102, respectively, contact external pads (not shown) on end 84 to provide electrical connection between terminals 100 and 102 and sensing element 80. Ends 104 and 106 of terminals 100 and 102, respectively, are maintained against second end 84 of sensing element 80 by a compressive force applied by disposing second end 84 of sensing element 80 between lower ends 104 and 106. Preferably, terminals 100 and 102 comprise spring terminals, as is known in the art, such that the compressive force generated by disposing second end 84 between spring terminals 100 and 102 securely maintains end 84 in electrical contact therewith. While spring terminals are disclosed herein, other known terminals that allow an electrical connection may be used.

Adjoined and partially encased by a bottom portion of upper shield 20, inner shield 40 has a first end 42 and a preferably partially closed second end 44 opposite first end 42. A centrally located annular opening 46 is provided at second end 44 and is sized to allow insertion of element second end 84 of sensing element 80 therethrough. Disposed within inner shield 40 is a central portion 83 of sensing element 80, and a high temperature material 90. Optionally, a pair of thermal insulating members (not shown) may be disposed against the sensing element 80 for additional support as is known in the art.

To allow an electrical connection of sensing element 80, a terminal connecter 60 can be used. The use of terminal connector 60 is known in the art and a suitable terminal connector 60 is also known in the art as an edge card connector, a clam shell connector, or the like. Terminal connector 60 typically includes a plurality of electrical terminals with each having a corresponding electrical wire connected thereto.

For the purpose of illustration only, sensor 10 is shown having a pair of electrical terminals 100 and 102, which are adapted to be connected to electrical wires 120 and 130 in a known manner. Electrical wires 120 and 130 pass through cable seal 140, which generally comprises an elastomeric material suitable for use in a high temperature environment, e.g., spark ignition engine, without failing. Cable seal 140 is maintained in place by upper shield 20, which has an upper end 23 forming a seal around a shoulder 142 of cable seal 140, wherein upper shield 20 can be crimped in place around cable seal 140 to further secure the same. A central portion 24 of upper shield 20 is disposed around terminal connector 60 while a lower end 22 of upper shield 20 forms an opening preferably tightly fit around inner shield second end 44 when sensor 10 is assembled. Generally, the upper shield 20 has a geometry complimentary with the inner shield geometry, such as cylindrical, elliptical, multi-sided, or the like.

In a generally preferred configuration, lower shield 30 is securely coupled to shell 50 by engaging flared open end 32 of lower shield 30 with annular recess 57. Shell 50 is itself securely coupled to upper shield 20 and thereby to optional inner shield 40 which is further secured by shoulder 56. Consequently, sensing element 80 is disposed through inner shield 40 with a first end 82 extending within sensing chamber 31. Lower shield 30 defines sensing chamber 31 and disposed within lower shield 30 can be an internal shield 35, which has an open end 36 for receiving sensing element 80 and a closed end 37 adjacent and parallel to closed end 34 of lower shield 30. Lower shield 30 and internal shield 35 incorporate a plurality of apertures on lower shield 38 and on inner shield 40 for allowing passage of exhaust gas in and out of sensing chamber 31 so that the gasses may be sensed by receptive first end 82 of sensing element 80.

Extending from first end 42 to partially closed second end 44, a high temperature material 90 can be concentrically disposed around sensing element 80. As used herein, the term "high temperature material" refers to materials that are designed for use in a spark ignition engine environment, where temperatures range up to about 1,000° C. Such materials include ceramic fibrous materials, and/or metal mesh, among others. When a ceramic fibrous material is used, the orientation and size of the ceramic fibers are not critical to the practice of the present invention. High temperature material 90 may be installed in either a preform or fibrous blanket type state around at least a portion of sensing element 80 as is known in the relevant arts.

Exhaust erosion of high temperature materials 90 and terminal connector 60 may be prevented in a particularly advantageous embodiment, which further comprises a disk supporting device and/or a metal mesh support, distinct from the high temperature material. These supports are capable, individually or in tandem, of providing secure support of the sensing element in the weak axis direction, and of preventing excessive exhaust erosion of sensitive sensor components.

The, disk element support 170 is positioned between partially closed second end 44 of inner shield 40 and mat 90, concentrically around sensing element 80. Disk element support 170 may also (or alternatively) be positioned between shoulder 56 of shell 50 and mat support 90. Also, an aperture is provided therein, through which the sensing element 80 may be inserted.

Disk element support 170 is made of a material compatible with the environmental conditions of the sensor. Specifically, the disk element support 170 is capable of maintaining structural integrity in a high temperature environment (up to about 1,000° C.). Exemplary materials include metal, ceramic, talc, composites, combinations combining at least one of the foregoing and others compatible with the sensor environment.

The mesh is typically located between high temperature material 90 and sensing chamber 31. The mesh can be made from fine wire, impregnated with a filler material, e.g. clay, talc, or the like, to fill the space between the mesh fibers, and compressed into desired form.

Wire material may be made of any metal, however, metals with high nickel or chrome content are preferred due to their rust resistant properties. Particularly preferred metals include 310, 309, and 316 stainless steels. Suitable thickness for fine wire material used as a mesh element support is about 0.2 to about 1.2 millimeters, with about 0.4 to about 0.6 millimeters being preferred. Preferred wire densities are about 20% to about 50% of the solid density, with the filler material making up the difference, giving a solid density of about 50% to about 70%.

As to the sensor's other materials, exemplary materials for the shields 20, 30, 40, and 35 and for the shell 50 include high chrome, high nickel stainless steel, or mixtures thereof, and the like, with all steels chosen for high temperature endurance, high-strength and corrosion resistance. Terminal connector 60 may be formed of a thermoplastic or thermoset material (e.g., plastic) or ceramic durable in the high temperature environments to which exhaust sensor 10 is exposed.

The present invention describes a new sensor and upper shield design and method of making the same. The crimp formed between upper shield 20 and shell 50 reduces the amount of pressure directed inward towards sensor element 80 during production. With the reduced stress, the sensor formed is less likely to fail and/or be scrapped. Furthermore, a more robust and simplified product can be produced that is less likely to leak from the adjoining of upper shield 20 to shell 50. This is because the crimp forms only a single sealing surface between upper shield 20 and shell 50, reducing potential leak points.

While preferred embodiments have been shown and described, various modifications and substitutions may be made thereto without departing from the spirit and scope of the invention. Accordingly, it is to be understood that the present invention has been described by way of illustration and not limitation.

What is claimed is:

1. An exhaust gas sensor, comprising:
   an upper shield having an upper shield first end and an upper shield second end;
   a shell having an inner edge, a shell first end, and a shell second end, said shell first end has a projecting edge, wherein a segment is formed between said projecting edge and inner edge;
   a bent portion of said projecting edge of said shell about a terminal end portion of said upper shield second end, wherein a terminal end portion of the upper shield second end rests on the segment;
   an inner shield positioned within said upper shield second end and said shell;
   a lower shield affixed to said shell second end; and
   a sensor element extending from said upper shield, through said shell into said lower shield.

2. The exhaust gas sensor of claim 1, wherein one or more gaskets are disposed between said bent portion and said terminal end portion of said upper shield second end.

3. The exhaust gas sensor of claim 2, wherein said gasket is an S-type gasket.

4. The exhaust gas sensor of claim 1, wherein at least one of said upper shield, said inner shield, and said shell comprise high chrome stainless steel, high nickel stainless steel, or mixtures combining at least one of the foregoing.

5. A method of forming an exhaust gas sensor, comprising:
   providing an upper shield having an upper shield first end and an upper shield second end;
   positioning an inner shield within a portion of the upper shield second end;
   providing a shell having an inner edge, a shell first end, and a shell second end, said shell first end has a projecting edge spaced apart from said upper shield, wherein a segment is formed between said projecting edge and said inner edge, wherein a terminal end portion of the upper shield second end rests on the segment;
   forming a bent portion by bending at least a portion of said projecting edge of said shell about a terminal end portion of said upper shield second end;
   affixing a lower shield to said shell second end; and
   extending a sensor element through said upper shield, through said shell into said lower shield.

6. The method of forming an exhaust gas sensor of claim 5, wherein said forming of said bent portion produces a single sealing surface between said upper shield, said inner shield, and said shell.

7. The method of forming an exhaust gas sensor of claim 5, further comprising:
   positioning one or more gaskets on said projecting edge of said shell prior to said forming of said bent portion.

8. The method of forming an exhaust gas sensor of claim 7, wherein said gasket is an S-type gasket.

9. The method of forming an exhaust gas sensor of claim 5, wherein at least one of said upper shield, said inner shield, and said shell comprise high chrome stainless steel, high nickel stainless steel, or mixtures combining at least one of the foregoing.

10. The method of forming an exhaust gas sensor of claim 5, wherein said forming of said bent portion comprises:
    applying pressure upon said projecting edge of said shell in a downward direction, parallel to said sensor element.

11. The method of forming an exhaust gas sensor of claim 10, wherein said pressure applied is about 10,000 p.s.i. to about 20,000 p.s.i.

12. The method of forming an exhaust gas sensor of claim 10, wherein said pressure applied is about 14,000 p.s.i. to about 16,000 p.s.i.

13. An exhaust gas sensor, comprising:
    an upper shield having an upper shield first end and an upper shield second end;
    a shell having an inner edge, a shell first end, and a shell second end, said shell first end has a projecting edge, wherein a segment is formed between said projecting edge and inner edge;
    a bent portion of said projecting edge of said shell about a terminal end portion of said upper shield second end, wherein a terminal end portion of the upper shield second end rests on the segment;
    an inner shield positioned within said upper shield second end and said shell;
    a lower shield affixed to said shell second end; and
    a sensor element extending from said upper shield, through said shell into said lower shield;
    wherein said bent portion produces a single sealing surface between said upper shield, said inner shield and said shell.

14. The exhaust gas sensor of claim 13, wherein one or more gaskets are disposed between said bent portion and said terminal end portion of said upper shield second end.

15. The exhaust gas sensor of claim 14, wherein said gasket is an S-type gasket.

16. The exhaust gas sensor of claim 13, wherein at least one of said upper shield, said inner shield, and said shell comprise high chrome stainless steel, high nickel stainless steel, or mixtures combining at least one of the foregoing.

* * * * *